United States Patent
Freeland

Patent Number: 5,152,290
Date of Patent: Oct. 6, 1992

[54] METHOD FOR RECORDING ULTRASOUND IMAGES TO DIAGNOSE HEART AND CORONARY ARTERY DISEASE

[75] Inventor: John C. Freeland, Boulder, Colo.

[73] Assignee: Prism Imaging, Inc., Broomfield, Colo.

[21] Appl. No.: 654,758

[22] Filed: Feb. 13, 1991

[51] Int. Cl.$^5$ .............................................. A61B 8/00
[52] U.S. Cl. ........................ 128/660.07; 128/661.04; 128/660.04
[58] Field of Search ...................... 128/660.04, 660.07, 128/661.07, 661.01; 73/861.25, 861.26

[56] References Cited

U.S. PATENT DOCUMENTS

| | | | |
|---|---|---|---|
| 4,593,314 | 6/1986 | Siler | 128/661.04 |
| 4,846,188 | 7/1989 | Yoshioka | 128/661.01 |
| 4,865,040 | 9/1989 | Ogasawara | 128/661.04 |
| 4,966,150 | 10/1990 | Etienne et al. | 128/661.04 |
| 5,016,642 | 5/1991 | Dukes et al. | 128/660.07 |

*Primary Examiner*—Kyle L. Howell
*Assistant Examiner*—George Manuel
*Attorney, Agent, or Firm*—John R. Ley; Robert G. Crouch

[57] ABSTRACT

Heart performance is evaluated by collecting ultrasound images of at least one chamber of the heart of a patient after peak exercise. The images are subsequently displayed and analyzed to determine the presence and degree of heart disease, such as coronary artery disease (CAD). Collecting the images is done continuously at a rate of at least eight images per heart beat synchronized to a predetermined point in each heart beat over a time period which is normally sufficient to capture ischemic events resulting from the peak exercise. Each image thus synchronized represents a similar condition of each heart beat, thereby facilitating accurate comparisons. Collecting of images can be interrupted to eliminate blank or obscured images while the ultrasound sensor is repositioned. The collected images can be displayed and subsequently analyzed to determine the presence and degree of heart disease by comparing the images from successive heart beats.

22 Claims, 4 Drawing Sheets

Fig_1

Fig_2

Fig_3

Fig_4

METHOD FOR RECORDING ULTRASOUND IMAGES TO DIAGNOSE HEART AND CORONARY ARTERY DISEASE

This invention relates to evaluating heart performance and specifically to the diagnosis of heart disease, such as coronary artery disease, with the aid of ultrasound imaging. More particularly, the present invention relates to a new and improved method for capturing and displaying ultrasound images of the heart for subsequent use in the diagnosis of heart disease.

BACKGROUND OF THE INVENTION

The most common disease of the heart is coronary artery disease (CAD). With coronary artery disease, an insufficient amount of blood flows to the heart muscle which contracts to produce the pumping action. Increased exercise or shock requires the heart to pump faster in order to distribute more oxygenated blood to the body in a given time. Under such circumstances, the heart muscle needs increased blood flow to function properly. With the constricted blood flow due to the presence of CAD, the heart muscle does not get enough blood and malfunctions in either a continual or intermittent fashion under stressful circumstances, while performing adequately under non-stressed conditions. The malfunction may manifest itself as a reduced ability to contract the heart chambers sufficiently to adequately increase blood flow. The amount of reduction indicates the degree or severity of the disease. An intermittent malfunction, known as an ischemic event, can be very brief, e.g. a few heart beats, or can be longer in more progressed states of disease. The term heart beat, as used herein, refers to one complete pumping cycle of the heart.

The effectiveness of detecting heart malfunctions and diagnosing CAD can be rated in terms of sensitivity and specificity. Sensitivity is a measure of a particular diagnostic ability to detect an event related to a heart malfunction. For example, a method with higher sensitivity is more likely to detect an ischemic event. Specificity is a measure of the ability to pinpoint the exact cause and location of the ischemic event, e.g. seventy percent blockage of the left coronary artery. It is desired that the initial tests used for diagnosing heart disease be as sensitive as possible to check for the presence of CAD, while tests pertaining to specificity may be more intensive after the disease has been detected.

One widely used technique for monitoring heart performance is an electrocardiogram (EKG), used in conjunction with a stress test. A stress test normally involves monitoring the heart performance before, during and after the patient experiences a drug-induced heart rate increase or performs a controlled exercise, e.g. cycling on a stationary bicycle or running on a treadmill. The stress test attempts to create exercise and stress conditions during which a diseased heart will not function properly. The EKG displays or records the electrical nervous signals supplied to the heart to cause it to beat. However, the EKG does not convey significant information regarding the movement or performance of the heart muscles in response to these signals.

A significant improvement in the ability to detect CAD resulted from the use of ultrasound imaging devices to observe a moving muscle wall of the heart. By definition, ultrasound is a sound pressure wave signal having a frequency greater than twenty kilohertz. An ultrasound transducer, which converts an electrical signal to a transmitted ultrasound wave and then converts the reflected ultrasound wave back to an electrical signal, is placed over the area of interest in a patient's body. In the case of diagnosing heart disease, the area of interest is, for example, the base or apex of the heart for observation of segments or sections of the left ventricle. A two-dimensional image is generated by sweeping the transmitted ultrasound wave through a fixed angle, the reflections from which are processed as a wedge or sector shaped image. The image generated is essentially a real-time image since the delays involved in receiving and processing the reflected ultrasound wave into the image therefrom are negligible.

Further improvements in the field of using ultrasound to monitor heart performance involved the addition of a recording capability, in order to preserve the ultrasound images. Videotape was used, as well as a device known as a Video Sheet Recorder (VSR), which records continuously for up to 10 seconds onto a disc shaped pieced of magnetic storage material similar to the magnetic tape used in video tapes. The advantage of a video sheet over a video tape is the ease with which a portion of the sheet can be replayed, since no rewinding is necessary. With both of these recording devices, images of the heart are continuously recorded in all states or phases of the heart beat cycle rather than synchronized to a particular point or points in the cycle. Continuous recording of the images does not readily lend itself to the type of comparisons which are advantageous enough for detecting CAD with a high degree of sensitivity. Since CAD manifests itself by a reduced compression effect of the heart chambers, it is desirable to observe and compare a series of images of the compression segments from successive heart cycles for successful diagnosis. Since the continuous, non-synchronized images obtained over the relatively short time period of ten seconds makes it difficult to compare successive heart cycles at similar conditions over a sufficient time to detect ischemic events, the sensitivity of the VSR device has not generally been regarded as sufficient for adequate detection of CAD.

A further improvement to the field of using ultrasound to monitor heart performance was realized in a device which senses the electrical nerve signal sent to the heart and uses this signal to synchronize the acquisition of images. A series of images from predetermined points in each of four successive heart beats is acquired and temporarily preserved. Eight images, generally equally spaced apart in time, are obtained of each heart beat cycle beginning with an image of the heart in the diastolic state and ending with an image of the heart in the systolic state. This series of images from one heart beat cycle represents the performance during compression of the heart chamber and is called an image loop. A display showing four images simultaneously (a quad-image) provides corresponding images of the same synchronized points from the preceding four heart cycles. After acquiring the four images, the operator quickly reviews the four heart beat cycles. This is done by scanning through the four image loops which are displayed in quad-image format, resulting in the simultaneous display of the corresponding images of the four image loops from the previous four heart beats. If desired, the operator may record the quad-image group in memory. The operator then repositions the sensor, if necessary, and acquires another quad-image group which must be similarly reviewed, and so on. While the transducer is removed and/or the four acquired heart beat cycles in the quad-image group are reviewed, the heart continues to beat and image loops of these beats are not acquired or observed. If an ischemic event occurs during this time, it is missed and not recorded. If the operator acts quickly and with facility to review the images, to record them, and to reposition the sensor in two seconds, only a few beats are missed, e.g. five, assuming a heart rate of one hundred-fifty beats per minute. Therefore, at about the quickest usage rate possible, image loops of four heart beats are acquired for every five heart beats for which no image loops are acquired. The number of non-acquired image loops becomes even greater with less accomplished operators who take longer times between acquisitions. Since an ischemic event may occur randomly and intermittently even under stress conditions, there is a significant possibility that previous devices may fail to provide the necessary sensitivity to detect CAD or other heart disease.

It is with regard to these and other considerations, and the desire to increase the sensitivity or likelihood of detecting ischemic events which are indicative of CAD and other heart disease, that the present invention has resulted.

SUMMARY OF THE INVENTION

The present invention allows the continuous recording of synchronized image loops of each successive heart beat over a time period normally sufficient to acquire an image of an ischemic event, thereby avoiding or reducing the possibility that ischemic events will not be observed. The image loops are subsequently displayed in a successive fashion to allow for the detection of ischemic events which are indicative of coronary artery disease. Images of the heart beat are not lost during the time period spent reviewing, recording and repositioning the transducer between successive acquisitions as with prior devices.

In accordance with one significant aspect of the present invention, a method for recording ultrasound images to diagnose heart disease, especially coronary artery disease, involves automatic recording of successive synchronized image loops of the heart beat into memory without the need for operator intervention, after positioning of the transducer. Once the operator has positioned the ultrasound sensor over the region of interest and initiated recording, the recording is continuous without interruption until the memory is full or the operator terminates recording. The capacity of the memory is sufficient to store an image loop from each heart beat during the time period commencing after peak exercise until past the point where an ischemic event would normally occur, for example about 80 seconds.

In accordance with another significant aspect of the present invention, the operator can pause the recording of images while the sensor is repositioned and re-initiate the recording of images when the sensor is again receiving good images of the area of interest. Thus the memory is efficiently filled with useful images rather than storing blank or poor images when the sensor is not adequately positioned.

In accordance with another significant aspect of the present invention, after the recording session is completed the operator and/or physician can quickly scan through the image loops of each of all of the recorded heart beats by viewing the image loops from each of four successive beats in groups of four on a quad-display. By viewing the heart beats in this way, comparable conditions of all of the successively recorded heart beats can be observed to more readily detect an ischemic event.

A more complete understanding and appreciation of the present invention can be obtained by reference to the accompanying drawings, which are briefly described below, from the following detailed description of the presently preferred embodiment, and from the appended claims.

DETAILED DESCRIPTION

A presently preferred embodiment of a conventional ultrasound apparatus 10 for generating ultrasound images, used together with an apparatus 15 for recording and displaying synchronized images to diagnose coronary artery disease or heart disease in practicing the present invention under the circumstances explained below, is shown in generalized form in FIG. 1. Much of the hardware used in practicing the present invention is known in the art and is discussed in a co-pending U.S. application by the same inventor, Ser. No. 07/613,318 filed on Nov. 8, 1990, entitled "Blood Pool Imaging and Analysis Technique Using Ultrasound," assigned to the assignee hereof.

In general the conventional ultrasound apparatus 10 includes a transducer 20 which is positioned on the skin of a patient (not shown). The transducer 20 emits or transmits ultrasound pulses in response to the application of electrical pulse signals 22 from a transmitter 24. The transmitted ultrasound pulses project into the patient's body where they encounter various structures, tissues, components and particles that cause a reflection or "echo" of the emitted ultrasound pulses back to the transducer 20. The echo ultrasound pulses contain information regarding the location and movement of the structures, tissues, components and particles which cause the echo. The transmitted pulses and the received echo ultrasound pulses form a beam 26 which scans through an angular sector 28 in a plane. The scanning effect is achieved by a scan signal 30 which is also transmitted from the transmitter in synchronism with the pulse signal 22. The scan signal causes either a mechanical movement of the transducer 20 or a deflection of the transmitted pulses from the transducer.

The ultrasound echo pulses are received by the transducer 20, and the transducer converts the echo pulses into an electrical echo signal 32. The echo signals 32 are applied to a receiver and digital scan converter 34. The receiver and converter 34 utilizes the information from the echo signal, the pulse signal 22 and the scan signal 30 to develop the ultrasound image information which will be presented, usually in enhanced form, by the ultrasound apparatus 10. The relative timing relationship of the emitted and echo pulses is employed to develop range or distance information by which to obtain information only from a selected range of interest or location in the Position information representative of the patient's body. Position information representative of the location of the object causing the reflection is developed by use of the scan signal 30. The position information is initially developed in a polar coordinate, two dimensional form due to the direct relationship of the range information relative to the angular sector 28. The position and range information constitute image information over the angular sector 28. The ability of ultrasound apparatus to provide this type of information is well known.

The digital scan converter aspect of the unit 34 converts the image information into digital scan signals which are supplied on a bus 36. The digital scan signals are obtained in incremental time segments and are typically assigned to successive or sequential locations in a memory 40 of a computer formed by a processor 38 and the memory 40.

Much of the signal processing necessary to obtain the range and position information contained in the image information may be obtained from the inherent functionality of the receiver of the unit 34. However, some of or all of this signal processing capability may be accomplished by the computer formed by the processor 38 and the memory 40 which are also connected to the bus 36. The image, range and position information available from the receiver and converter 34 is stored in the system memory 40.

With many modern ultrasound apparatus, the image information may also be subjected to certain well known image enhancing operations in which the computer subjects the image information to image enhancing algorithms in order to obtain a more useful display of actual conditions free from some of the spurious effects which are inherent in ultrasound imaging. A variety of known algorithms are used to determine from the signals recorded in memory, the edges and other characteristic features represented by the data. These algorithms are known by various titles, and are readily available for use by those skilled in this field. In any event, the computer typically utilizes such algorithms under software control to derive the enhanced images. Usually the image information will be enhanced before it is recorded in memory.

A display 42 visually presents the real-time image information to the user. Typically the display will be a CRT or raster scan device, and the user may manually select a variety of information to be displayed, by signals derived from a keyboard or other control device (not shown) connected to an I/O interface 48. The information to be displayed is selected from the memory 40, and it is supplied to a video converter 44 which is also connected to the bus 36. The video converter 44 converts the information from digital form to an analog video format signal 45 and supplies it to the display 42. The video converter supplies the analog video signal 45 in one of a variety of different known video formats. Typically, the analog video signal 45 carries image information at a rate of thirty frames or images per second.

The transmitter 24 is also connected to the bus 36 and can also be controlled by the computer, if desired, when generating the pulse and scan signals 22 and 30 respectively. The pulse and scan signals are generated continuously and are not synchronized to the patient's heart function. For the operator's convenience a conventional electrocardiograph (EKG) signal 46 is supplied from an electrode or sensor attached to the patient. The signal 46 is generated from the electrical signal conducted to the nerves of the heart in order to cause the muscles to contract and beat. A signal corresponding to the EKG signal 46 is supplied to the bus 36 through the conventional I/O interface 48. The EKG information is provided on the display 42.

The present invention is preferably practiced by using the conventional ultrasound apparatus 10 together with the apparatus 15 for recording and displaying synchronized images, although a single device having the necessary functionality of both apparatus 10 and 15 could be devised within the scope of the present invention. The recording and displaying apparatus 15 includes a video converter 55 which converts the analog video signal 45 into digital form, and supplies the digital signal to a bus 58. Alternatively, the image information could be passed from the bus 36 to the bus 58 via an interface such as the I/O interface 48 of the conventional apparatus 10 and an I/O interface 72 of the recording and displaying apparatus 15. A processor 60 controls the recording of the image information on the bus 58 into a video storage unit or device 65. This video storage unit may be comprised of digital memory, or an optical, magnetic or magneto-optical storage device. An I/O device 70 supplies external commands and signals for controlling the apparatus 15 by accessing the bus 58 through the I/O interface 72. The bus 58 allows the processor 60 to control the video storage unit 65 and the video converter 55. The video converter 55 also can obtain image information from the video storage unit 65, convert the information from digital form to analog video format signals 74 and supply them to a display 75. The analog signals 74 may be in one of a variety of different known video formats. The I/O device 70 may be comprised of a computer keyboard or hardware control switches, for example, which control the operation of the apparatus 15. A memory 76 of a computer formed by the processor 60 and the memory 76 stores software instructions and data for use by the processor 60.

The EKG signal 46 is also provided to the apparatus 15 through the I/O interface 72. This EKG signal 46 is used by the computer of the apparatus 15 to synchronize or trigger the recording in the video storage unit 65 of image information representative of predetermined points in the heart beat of the patient, preferably with relation to the R-wave of the EKG signal 46.

By triggering the recording of image information relative to a synchronized point in the heart beat, frames or still images of the heart from similar points in consecutive cycles are obtained. Each frame includes the composite of all of the digital signals recorded in the video storage unit 65 derived from a single scan. With the present invention, an image loop is preferably made up of eight to sixteen images from each heart beat. If the apparatus 10 acquires images at a rate greater than the rate at which the apparatus 15 records the selected number of images in the image loop, the image information supplied by the video converter 44 is captured or selected to most nearly coincide in time with the time interval of the number of images forming the image loop for each heart beat derived by the apparatus 15. In this manner enough image loops of consecutive heart beats are obtained over a sufficiently long time period to normally capture any ischemic event which may occur after peak exercise, e.g., at least eighty seconds or over two hundred heart beats.

One of the operator generated control signals at the I/O device 70 is a "record"/"pause" signal. This signal is generated by the operator through the I/O device 70 either to command that the processor 60 continuously record or store images into the video storage unit 65 (record), or alternatively, to temporarily stop the recording process (pause). During an image viewing session, four image loops from four consecutive heart beats are displayed simultaneously (FIG. 2) in the quad-display format. As stated above, the images of each of the four image loops are corresponding views of the heart taken from approximately the same synchronized points in each of four successive heart beats. These sets of four image loops are called quad-image groups. A "next quad-image group"/"previous quad-image group" signal may also be generated by the operator through the I/O device 70 to select the next or previous quad-image group for viewing and analyzing. In this manner the operator is able to scan through and review all of the image information.

The operator can also generate, through the I/O device 70, several other signals. One signal is a command to select the number of images recorded in each image loop. This number may vary from eight to sixteen images. When the apparatus is asked to record more than eight images in each image loop there is, of course, an increase in the image information about each particular heart beat and a corresponding decrease in the number of image loops which may be recorded into the video storage unit 65. This increase of images per image loop may result in a storage capability of less than eighty seconds of image loops or heart beats, unless the capacity of the video storage unit is also increased.

Another signal which the operator can generate through the I/O device 70 is a "Last Chance" signal which commands the apparatus 15 to acquire four more image loops when the video storage unit 65 is full. The additionally acquired image loops are recorded in place of the previous last four image loops recorded. The operator can also generate signals through the I/O device 70 to terminate recording at any time during the recording process or to terminate displaying at any time during the displaying process. The operator can also generate a signal through the I/O device 70 to cause the apparatus 15 to begin the displaying process with a quad-image group other than the first acquired quad-image group. Other signals can be generated by the operator as needed and in accordance with software commands recorded in the memory 76.

Figure 1:
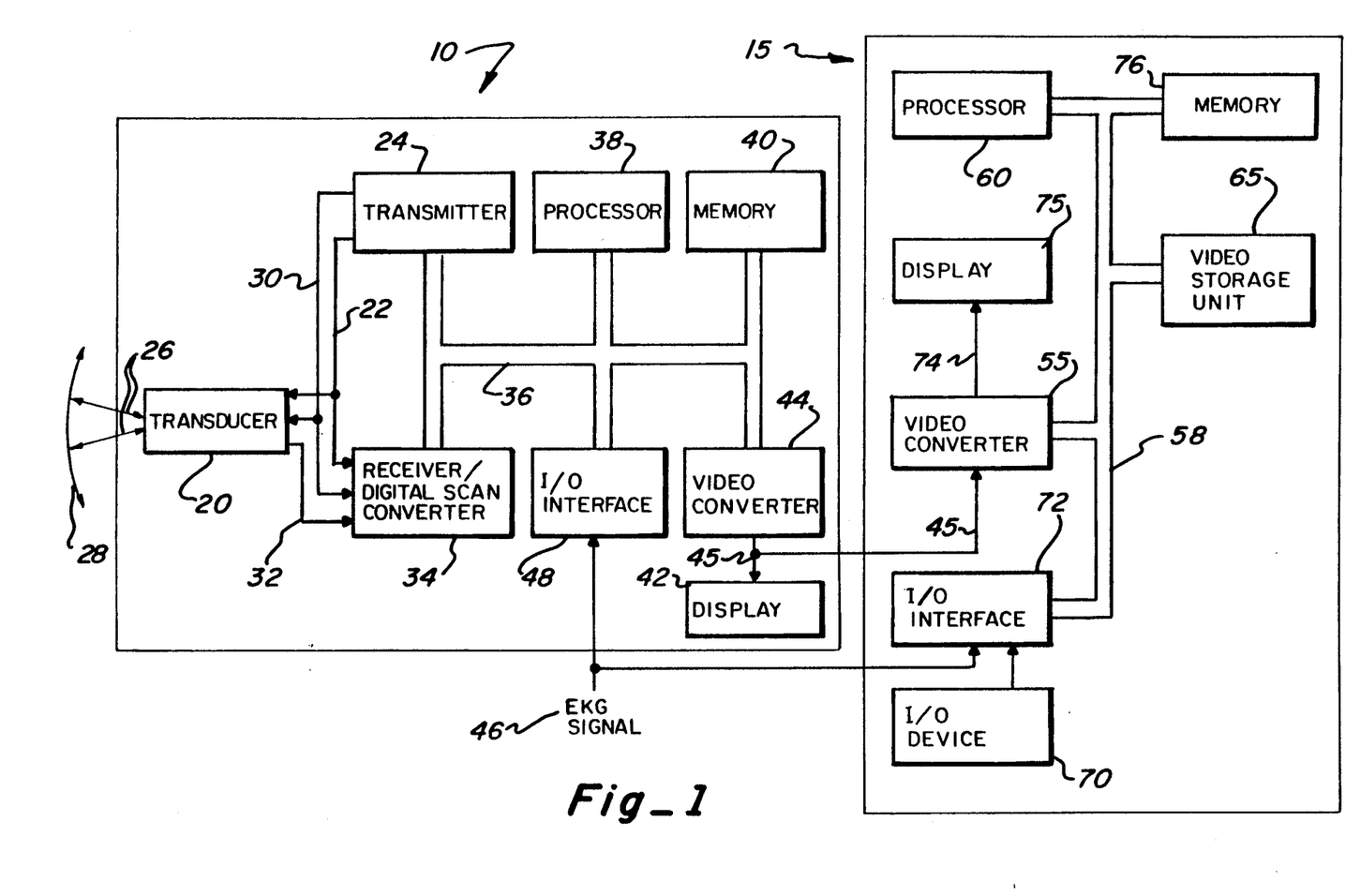
FIG. 1 is a block diagram of the components used in generating, recording and displaying ultrasound images to diagnose coronary artery disease or other heart disease, according to the present invention.
Figure 2:
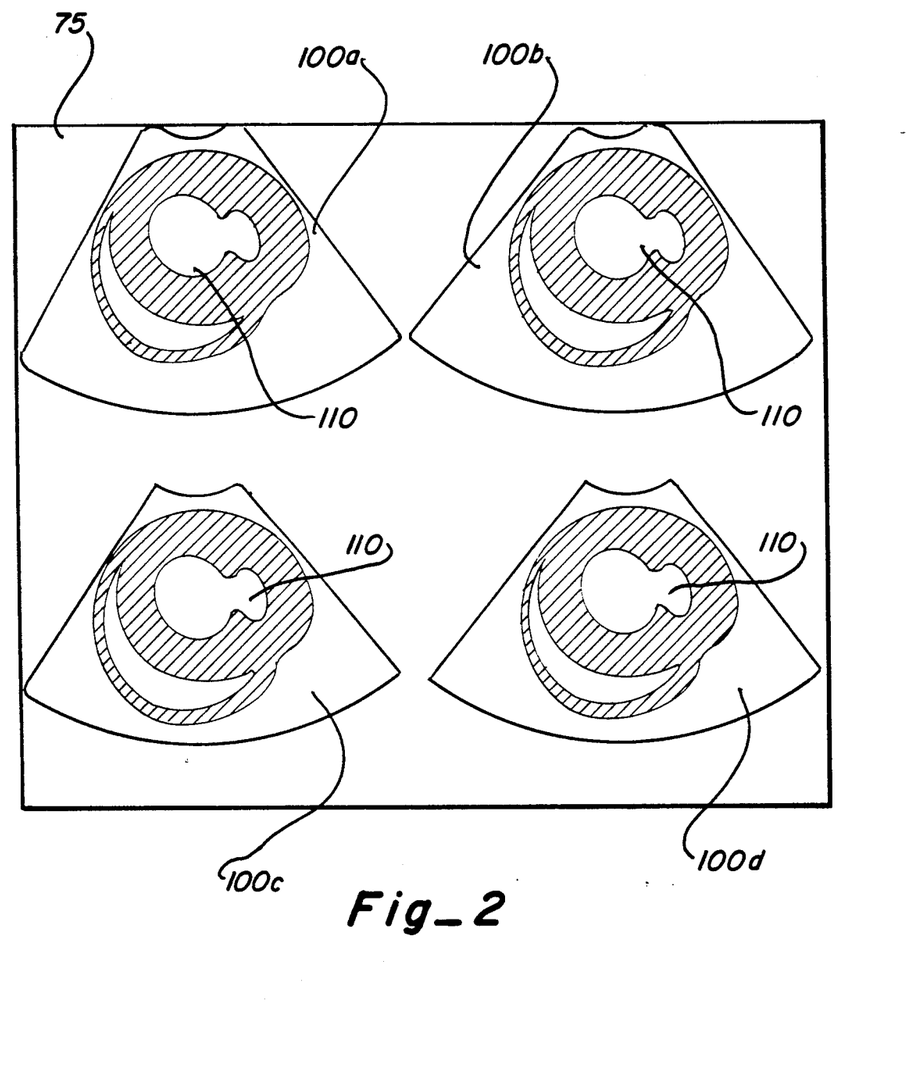
FIG. 2 is an enlarged illustration of a quad-display of the corresponding images from four image loops of four successive heart beats synchronously detected and recorded by the apparatus shown in FIG. 1.

The display 75 of the recording and displaying apparatus 15 shown in FIG. 1 can display the quad-image comprised of four images 100a, 100b, 100c and 100d as shown in FIG. 2. An outline 110 of a chamber of the heart can be seen in each image 100a, 100b, 100c and 100d. These outlines represent the state of the heart muscle at four corresponding points in four sequential heart beats.

Upon integrating the apparatus 10 and 15 into a single device in order to practice the present invention, some of the elements shown in FIG. 1 may be implemented in single devices. For example, in such a single apparatus, the processors 38 and 60, the memories 40 and 76, the busses 36 and 58, the I/O interfaces 48 and 72, the video converters 44 and 55, and the displays 42 and 75 may be implemented as single devices. A single I/O device could be used to control the single integrated apparatus. The advantage to the arrangement illustrated by FIG. 1 is that the separate apparatus can be used in conjunction with the pre-existing ultrasound apparatus 10. Furthermore, there may be times when the increased flexibility of separate apparatus 10 and 15 will be beneficial, such as when the apparatus is needed for examining image loops and the apparatus 10 is needed for another unrelated ultrasound procedure.

Figure 3:
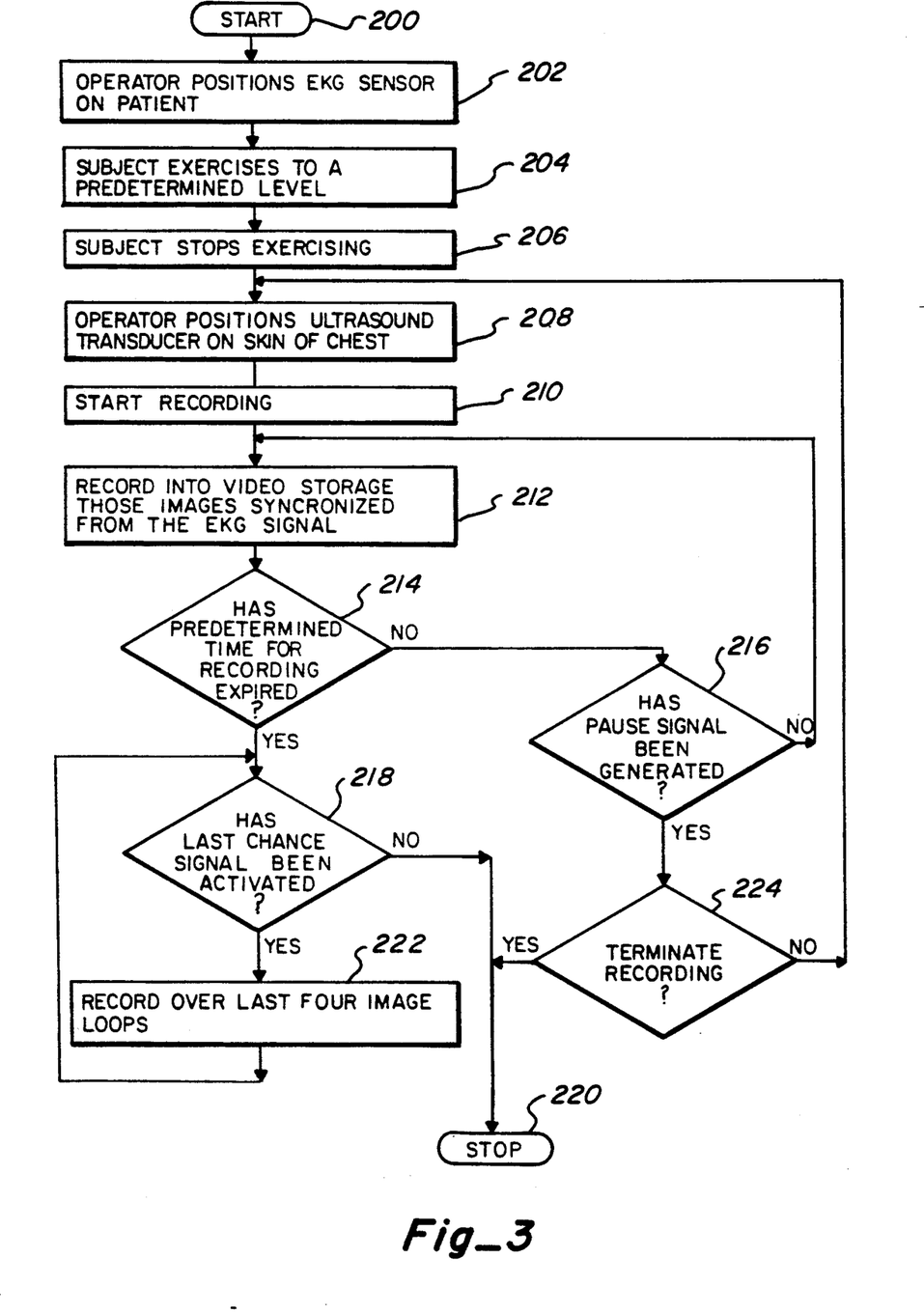
FIG. 3 is a simplified flow diagram of the operations performed in acquiring images with the aid of the apparatus shown in FIG. 1.

The procedure or sequence by which the images are obtained and recorded by the apparatus 10 and 15 shown in FIG. 1 is illustrated by the flow diagram in FIG. 3. To start (200) the sequence, the operator first positions an EKG sensor on the patient's skin (202). The patient exercises to a predetermined exercise level (204), which is sufficient generally to obtain a maximum or near maximum heart rate. This is most commonly done by running on a slightly inclined treadmill or by cycling on a stationary bicycle, but the heart rate can also be increased with drugs. After the predetermined exercise level is reached the patient stops exercising (206). Next, the operator positions the ultrasound transducer 20 on the skin of the chest adjacent the heart (208). The recording functionality is then started (210) by generating the record/pause signal. The EKG signal 46 triggers the apparatus 15 (FIG. 1) to record images taken at predetermined points in the heart beat, preferably in response to the R-Wave portion, as determined by the EKG signal (212).

Recording continues (212) until a sufficient number of image loops and heart beats normally necessary to detect an ischemic event have been obtained. This number of image loops has generally been determined to be related to a predetermined recording time period, preferably eighty seconds, at eight images per image loop. Of course, sufficient capacity in the video storage unit (65, FIG. 1) must be provided to accept and hold this number of images. So long as the predetermined time period has not been exceeded (214) and the pause signal has not been generated (216), the recording step (212) is repeated for each subsequent heart beat.

Once the predetermined time period has been exceeded (214), it is then determined whether the Last Chance signal has been activated (218). If the Last Chance signal has not been activated, then the procedure stops (220). If the Last Chance signal has been activated, then four more image loops are recorded (222) in the memory locations where the last four image loops had been stored. The procedure then loops back to determine if the Last Chance signal is still activated (218). This loop (218 and 222) continues until the Last Chance signal is de-activated, at which point the procedure stops (220).

If the operator generates (216) the pause signal, a determination is thereafter made (224) if the operator wishes to terminate recording and stop the procedure (220), or to reposition the ultrasound transducer (208) and again continue or start recording (210). Thus, it can be seen that if the operator generates the pause signal when repositioning the sensor no blank or poor images will be recorded. As a result, the video storage unit (65, FIG. 1) is filled with a series of intelligible images obtained relative to synchronized points from successive heart beats. These images can be viewed and analyzed immediately or at any subsequent time to look for ischemic events which would be symptomatic of coronary artery or other heart disease.

Preferably, the size of the video storage unit (65, FIG. 1) will hold image data from up to two hundred image loops at eight images per image loop. Assuming a heart rate of one hundred fifty beats per minute, the memory will hold approximately eighty seconds of image loops each containing eight images. As described, eighty seconds of heart beats and image loops appears sufficient to normally detect the vast majority of ischemic events which may occur after peak exercise from a stress test. Displayed in groups of four, this amount of information correlates to fifty quad-image groups. The operator and/or physician can readily scan through these image loops. Since the series of image loops providing individual images taken from similar points in the heart beat of a healthy heart recovering from peak exercise should show only a gradual change in the compression segment of the heart beat as the heart returns toward its normal non-stressed condition, an ischemic event, e.g. a heart chamber wall not moving normally, should be readily apparent from the compared image loops of the heart beats. At the end of the recording period, the scanning can then be stopped and the image loops or loops containing the ischemic event can be examined more closely.

Figure 4:
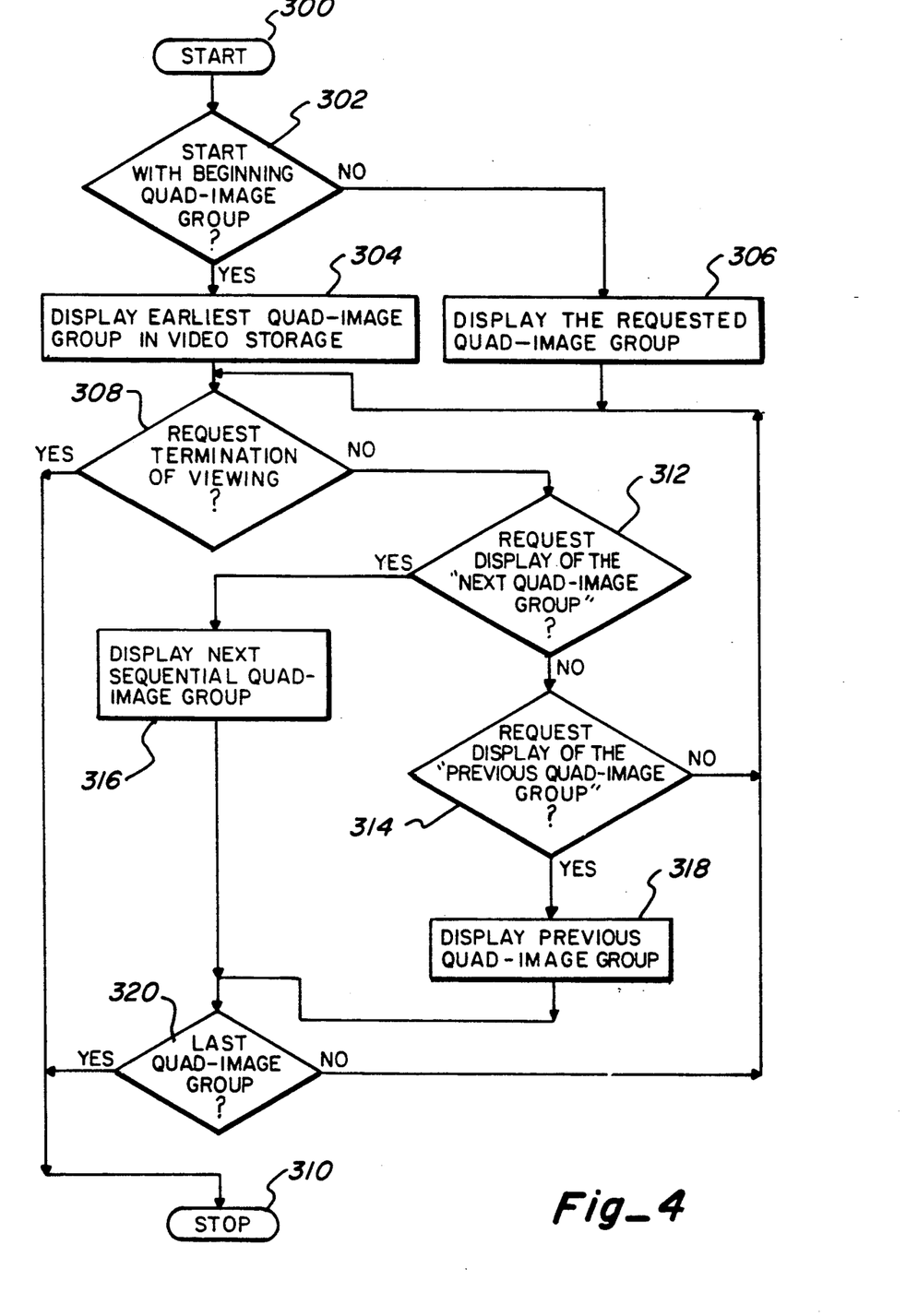
FIG. 4 is a simplified flow diagram of the operations performed in reviewing the images acquired by the apparatus shown in FIG. 1 in order to diagnose coronary artery disease or heart disease.

The preferred process by which the image loops are displayed or examined is shown in the flow diagram of FIG. 4. The process starts (300) by determining (302) whether to start the viewing session at the first quad-image group or at a quad-image group other than the first quad-image group. Upon starting at the beginning or earliest obtained quad-image group, that quad-image group is displayed (304). If the operator desires to start at another quad-image group, then that selected quad-image group is displayed (306).

Next, a loop (308 and 312 to 320) is entered which allows sequencing through the remaining quad-image groups. First, a determination is made (308) whether a request to terminate the viewing session has been generated. If so, the display and examination of image loops process stops (310). If not, a determination is made if a request to display either the next quad-image group (312) or the previous quad-image group (314) has been generated. If neither a request to display the next nor the previous quad-image group has been generated, a loop back occurs to determine if a termination has been requested (308). If none of the three requests (312, 314 or 308) has been made, the sequence will continue while displaying the same quad-image group. When the next quad-image group or the previous quad-image group is requested, either the next sequential quad-image group (316) or the previous quad-image group (318) will be displayed, respectively. Thus, it can be seen that the operator can quickly sequence forward or backward through the quad-image groups.

After the quad-image group is displayed, it is determined if the quad-image group displayed is the last quad-image group (320). If so, the display and examination of image loops process stops (310). If the changed quad-image group is not the last quad-image group, a loop back occurs to determine if a termination has been requested (308).

This improved method of acquiring and viewing images of the heart achieves a sensitivity of detecting ischemic events which is believed to be in the range of eighty to ninety percent. In contrast, the prior art techniques typically yield a sensitivity of under fifty percent because with the prior methods a significant number, for example, three to twenty heart beats are missed for every four acquired. There are two major factors which limit a greater sensitivity. The first factor is the number of heart beats missed when the operator pauses recording. As mentioned previously, with the present invention the operator may pause or interrupt the recording in order to reposition the transducer. The second factor is the number of obscured images of the heart. This factor may be due to artifact such as an expanding lung blocking the view of the heart or other body movement by the patient. This second factor can not be resolved by the present invention, but it can be understood that the present invention does provide for and significantly enhance the sensitivity in detecting heart disease such as CAD as a result of improvements with respect to the first aforementioned factor.

There exist differences in medical opinion regarding the time period which is sufficient to capture an ischemic event. While the preferred embodiment provides for a time period of eighty seconds of recording, there are physicians who believe a shorter time period, e.g. sixty seconds, is sufficient. Therefore, the present invention allows the operator to select the time period for recording. A much higher sensitivity in detecting heart disease such as CAD will result from the use of the present invention due to the considerably increased capacity for obtaining images, and the other described considerations.

A presently preferred embodiment of the present invention has been described above with a degree of specificity. It should be understood, however, that this degree of specificity is directed toward the preferred embodiment. The invention itself, however, is defined by the scope of the appended claims.

I claim:

1. A method of acquiring and displaying ultrasound images of at least one moving chamber of the heart to evaluate heart performance by observing any ischemic event in the movement of the at least one chamber after exercise, comprising:

obtaining an ultrasound image of the at least one chamber of the heart at a plurality of different predetermined points occurring during each one of a plurality of successive heart beats, whereby a plurality of images are obtained of each heart beat;

obtaining the images for a predetermined time period extending sufficiently long after exercise to capture an image of any ischemic event resulting from the exercise;

synchronizing the predetermined points at which each image of each heart beat is obtained to obtain corresponding images from corresponding different predetermined points during each heart beat by obtaining the images in relation to a predetermined common synchronizing point common to each one of the successive heart beats;

recording all of the ultrasound images obtained as a series;

displaying recorded images from the series in groups, each group containing images from a predetermined number of successive heart beats, the number of heart beats in a group being less than all of the heart beats for which images have been recorded in the series.

2. A method as defined in claim 1 further comprising:

obtaining at least eight images from each beat of the heart.

3. A method as defined in claim 1 wherein the predetermined time period is at least sixty seconds.

4. A method as defined in claim 1 wherein the predetermined time period is approximately eighty seconds.

5. A method as defined in claim 1 further including selectively interrupting the recording of the series of images.

6. A method as defined in claim 1 further comprising:
deriving information which describes each image obtained; and
recording in a video storage device the information which describes each image of the series.

7. A method as defined in claim 6 further comprising:
displaying each image by using the information recorded in the video storage device to create the image.

8. A method as defined in claim 1, further comprising:
displaying in each group the corresponding images from the heart beats of each group.

9. A method as defined in claim 8, further comprising:
displaying sequentially all of the corresponding images from each of the heart beats of each group.

10. A method as defined in claim 9, further comprising:
displaying another group of images after all of the corresponding images from the heart beats of the previously displayed group have been displayed sequentially.

11. A method of evaluating heart performance by observing changes revealed by ultrasound images of at least one chamber of the heart after exercise, comprising:
collecting information which defines a plurality of ultrasound images of the at least one chamber of the heart during successive heart beats;
collecting the information in synchronization to a predetermined synchronizing point common to each one of the successive heart beats;
storing the information in a video storage device;
continuously collecting and storing the information without interruption for a predetermined time period extending sufficiently long after exercise to normally capture any ischemic event resulting from the exercise;
displaying the ultrasound images by retrieving from the video storage device the stored information which defines the images;
using the retrieved information to create the display; and
comparing the displayed images collected from a plurality of successive heart beats to evaluate heart performance.

12. A method as defined in claim 11 further comprising:
collecting information which defines at least eight images from each successive heart beat.

13. A method as defined in claim 12 wherein the information defining the at least eight images from each heart beat is taken relative to the synchronizing point common to each heart beat.

14. A method as defined in claim 11 wherein the predetermined time period is at least sixty seconds.

15. A method as defined in claim 11 wherein the predetermined time period is approximately eighty seconds.

16. A method as defined in claim 11 wherein the images are simultaneously displayed in groups of images, each image group being a plurality of the images obtained and stored over the predetermined time period.

17. A method as defined in claim 16 further comprising:
analyzing the displayed images for changes of the one chamber of the heart; and
evaluating heart performance from the changes of the at least one chamber of the heart revealed by the displayed images.

18. A method as defined in claim 17 wherein each image group includes less than all of the images obtained and stored over the predetermined time period.

19. A method as defined in claim 16 wherein each image group includes a plurality of images, each image collected at a similar point in the cycle of a plurality of successive heart beats.

20. A method as defined in claim 16 wherein each image group includes less than all of the images obtained and stored over the predetermined time period.

21. A method as defined in claim 11 further comprising:
analyzing the displayed images by viewing the images to determine the presence and degree of coronary artery disease.

22. A method of evaluating heart performance by observing changes revealed by ultrasound images of at least one chamber of the heart after exercise, comprising:
collecting information which defines a plurality of ultrasound images of the at least one chamber of the heart during successive heart beats;
collecting the information in synchronization to a predetermined synchronizing point common to each one of the successive heart beats;
storing the information in a video storage device;
collecting and storing the information over a predetermined time period extending sufficiently long after exercise to normally capture any ischemic event resulting from the exercise;
displaying the ultrasound images by retrieving from the video storage device the stored information which defines the images;
using the retrieved information to create the display;
comparing the displayed images collected from a plurality of successive heart beats to evaluate heart performance; and
selectively interrupting the collecting and storing of the information which defines ultrasound images of the at least one chamber of the heart.

* * * * *